United States Patent
Ochoa et al.

[11] Patent Number: 5,935,172
[45] Date of Patent: *Aug. 10, 1999

[54] PROSTHESIS WITH VARIABLE FIT AND STRAIN DISTRIBUTION

[75] Inventors: Jorge A. Ochoa, Norton; Michael J. O'Neil, West Barnstable, both of Mass.

[73] Assignee: Johnson & Johnson Professional, Inc., Raynham, Mass.

[*] Notice: This patent issued on a continued prosecution application filed under 37 CFR 1.53(d), and is subject to the twenty year patent term provisions of 35 U.S.C. 154(a)(2).

[21] Appl. No.: 08/673,368

[22] Filed: Jun. 28, 1996

[51] Int. Cl.$^6$ ........................................ A61F 2/30
[52] U.S. Cl. .................. 623/18; 623/23; 623/16; 606/77
[58] Field of Search .................. 623/16, 18, 20, 623/22, 23, 66; 606/76, 77

[56] References Cited

U.S. PATENT DOCUMENTS

| | | | |
|---|---|---|---|
| 4,495,664 | 1/1985 | Blanquaert | 3/1.913 |
| 4,713,076 | 12/1987 | Draenert | 623/16 |
| 4,851,008 | 7/1989 | Johnson | 623/22 |
| 4,878,917 | 11/1989 | Krantz et al. | 623/18 |
| 4,976,736 | 12/1990 | White et al. | 623/16 |
| 4,990,161 | 2/1991 | Kampner | 623/20 |
| 5,007,931 | 4/1991 | Smith | 623/23 |
| 5,061,286 | 10/1991 | Lyle | 623/16 |
| 5,074,879 | 12/1991 | Pappas et al. | 623/23 |
| 5,152,795 | 10/1992 | Sioshansi et al. | 623/22 |
| 5,201,766 | 4/1993 | Georgette | 623/22 |
| 5,201,771 | 4/1993 | Belykh et al. | 623/23 |
| 5,258,034 | 11/1993 | Furlong et al. | 623/23 |
| 5,336,265 | 8/1994 | Serbousek et al. | 623/18 |
| 5,343,877 | 9/1994 | Park | 623/18 |
| 5,376,123 | 12/1994 | Klaue et al. | 623/16 |
| 5,458,653 | 10/1995 | Davidson | 623/18 |
| 5,507,828 | 4/1996 | Maumy et al. | 623/22 |
| 5,514,184 | 5/1996 | Doi et al. | 623/22 |
| 5,571,204 | 11/1996 | Nies | 623/23 |
| 5,679,294 | 10/1997 | Umezu et al. | 264/44 |
| 5,702,484 | 12/1997 | Goymann et al. | 623/23 |
| 5,725,590 | 3/1998 | Maumy et al. | 623/22 |

*Primary Examiner*—Michael J. Milano
*Assistant Examiner*—Tram A. Nguyen
*Attorney, Agent, or Firm*—Nutter, McClennen & Fish, LLP

[57] ABSTRACT

A joint prosthesis comprising a metallic body having a plurality of negative surface features such as through-slots, deep grooves, tunnels or pits, or valleys defined between projecting fingers or flutes. The metallic body constitutes the structural component of the prosthesis, such as a shell, plate or stem. A second part attaches to and extends the body to provide both a fit and a change in the initial stiffness. The second part provides a time-evolving structural coupling, such that the prosthesis initially fits the patient's remnant bone to provide rigid fixation, while the mechanical properties shift with time in vivo to change its contact or loading characteristics. In one embodiment a femoral stem joint prosthesis is modular and the first, or structural component, accommodates bio-absorbable second components of varying geometries and dimensions which fit a range of bore sizes, and achieve different stiffnesses or strengths affecting load or strain distribution.

7 Claims, 4 Drawing Sheets

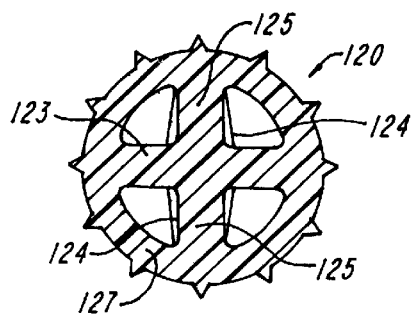
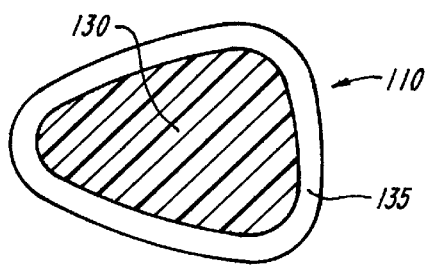
*FIG. 2B*  *FIG. 2C*
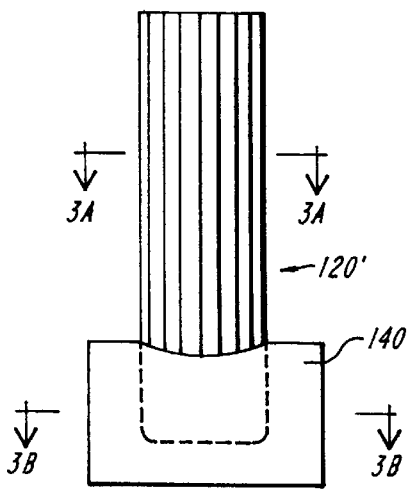
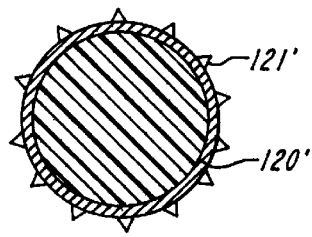
*FIG. 3*  *FIG. 3A*
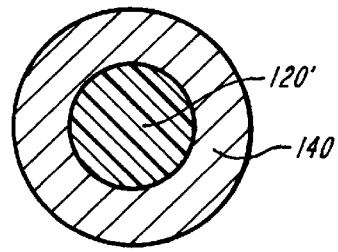
*FIG. 3B*
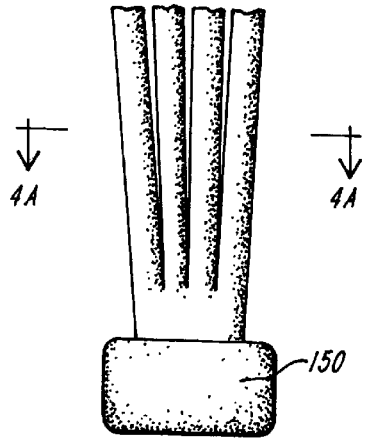
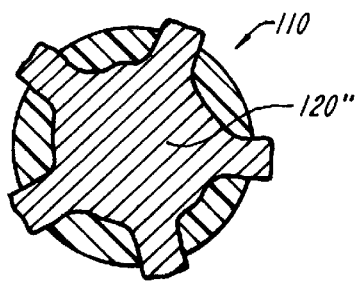
*FIG. 4*  *FIG. 4A*

PROSTHESIS WITH VARIABLE FIT AND STRAIN DISTRIBUTION

BACKGROUND OF THE INVENTION

The invention relates to implantable bone prostheses, and more particularly to joint prostheses that attach to bone and have properties, such as fit and fill, which change after implantation.

Joint prostheses are well known in the art and have long been used to replace natural joints, including knees, hips, shoulders, and elbows. Such prostheses may include a projecting part, such as a stem configured to mount in or attach to the remaining natural bone and secure the prosthesis. The size, shape and materials of a joint prosthesis are critical to ensuring proper fit within a patient's body, and may also affect the extent of bone growth into and surrounding the prosthesis, both of which contribute to fixation of the prosthesis within the patient.

Earlier versions of joint prostheses have relied extensively upon bone cements to fix a prosthesis within natural bone.

Cements provide the high degree of initial fixation necessary for healing following surgery but result in a very stiff overall structure, are prone to loosening with time, and can provoke tissue reactions or systemic responses. Nonetheless they remain widely used, although in current practice they may be applied over smaller regions than before, or be used in conjunction with other modes of fixation. Over the longer term, fixation now also relies on the provision of textured regions, and regions which enhance bone growth by providing a structure or framework of porous material, with or without coatings of bone-growth enhancement materials, such as hydroxyapatite or calcium oxide materials and various organic growth promoters, to bring about secure coupling by intergrowth of new bone material. In some constructions, a bio-absorbable material is also used to fill irregularities, allowing pores or cavities in a permanent metal body to open up and become filled in coordination with ongoing regeneration and ingrowth of the surrounding bone.

With these more complex constructions, resorption of a coating or filler, and its replacement by bone ingrowth can cause the properties of the prosthesis (e.g., stiffness) to change over time. For example, a particular joint prosthesis, such as a hip stem, may have a stiffness which is acceptable at the time of implantation, but which becomes either too flexible or too stiff subsequent to implantation as a result of bone ingrowth and dissolution of material. Conversely, engineering an implant with properties at levels which are desirable for the long term may result in a prosthesis which has properties that are not suitable at the time of implant.

Some attempts have been made to improve the fit and fill characteristics of joint prostheses during healing by regulating the timing of bone ingrowth, generally by selection of pore size and coating solubility.

U.S. Pat. No. 4,713,076 discloses a bone implant coating formed of a calcium-based filling material and a binding agent, both of which are bio-absorbable. The filling material is in the form of porous spherical particles with a diameter of about 10–200 micrometers and a pore volume of 25–80%. The ultrastructure of the coating is stated to promote rapid ingrowth of bone into the coating.

U.S. Pat. No. 5,258,034 discloses a hip stem prosthesis that provides controlled bone ingrowth. A bone ingrowth-promoting coating is provided at a proximal part of the prosthesis to promote rapid bone ingrowth at that region of the prosthesis. The distal end of the prosthesis, where rapid bone ingrowth is not desired, includes an absorbable coating or sleeve. The thickness of the absorbable coating or sleeve is designed to be absorbed over the period of time during which bone ingrowth at the proximal end of the femoral stem would normally take place.

U.S. Pat. No. 5,007,931 discloses a femoral stem implant in which longitudinal channels are made in the stem to reduce its section modulus, and elongated strips of a porous material are bonded only to the floors of the channels keeping destructive bending stresses low and avoiding notching. The stem is shaped for cementless fixation in a bore prepared in the femur.

Despite advances made thus far in the design of joint prostheses, there remains a need for a joint prosthesis in which the mechanical and physical properties of the prosthesis stay appropriate in different phases of the post-implantation period.

It is thus an object of the invention to provide a joint prosthesis in which mechanical and physical properties, including shape, size, stiffness, strength and density, vary over time in a controlled fashion after implantation.

A further object is to provide a joint prosthesis having physical and mechanical properties that evolve from a first plurality of properties which are advantageous at the time of implantation to a second plurality of properties which are advantageous at a later time.

A further object is to provide a joint prosthesis that possesses short term stiffness to promote good fixation, and evolves long term bending flexibility to improve its performance and useful life.

It is yet another object to provide a joint prosthesis that is modular in the sense that adjustments and modifications to the prosthesis are readily made by a surgeon in the operating room environment by interchanging or modifying components to tailor the device to a specific patient.

The attainment of these and other objects of the invention will be apparent to those skilled in the art upon reading the disclosure that follows.

SUMMARY OF THE INVENTION

The present invention achieves one or more of the foregoing objects by providing a joint prosthesis having a first part, including a body formed of metal or the like which is permanent and which constitutes the essential overall shape and structural component of the prosthesis, such as a shelf, plate or stem. The body has a plurality of negative surface features such as deep grooves, tunnels or pits, or valleys or slots defined between or within projecting walls, wings, fingers or flutes. A second part, which is non-permanent, is attached to the body, and provides both a fit, and a time-evolving structural coupling to surrounding bone, such that the prosthesis initially fits the patient's remnant bone, while the mechanical properties evolve and shift with time in vivo to change the position or distribution of its coupling to bone along its length.

In one aspect of the invention, illustrated by a femoral stem, the negative surface features formed in the body or structural component take the form of axially extending grooves made, for example, at the distal end of the metallic structural component or at a position intermediate the proximal and distal ends of the metallic structural component. The negative surface features can also include one or more transversely oriented grooves formed in the metallic structural component, or one or more bores formed in the metallic structural component. The negative surface features may also be defined by axial flutes in a beam-like structure, or by slots which separate the body into prongs or fingers. Preferably, the second part is a bio-absorbable component which is adhered to, frictionally engaged within or mechanically interlocked with the negative surface features and which thereby augments the structural body, for example, by increasing its size and/or bending stiffness, and forms a compound unitized prosthesis. The second part extends at least partially beyond or outside of the structural body to provide initial points of contact against surrounding bone in at least one region thus providing an initially rigid fixation.

In one embodiment, the joint prosthesis is a modular set and the structural component has formed therein one or more negative surface features that accommodate different ones of a selectable set of bio-absorbable inserts or attachments of varying geometries and dimensions. These second parts mechanically interfit with the structural component, and may come in a range of sizes or shapes such as wedges, or plugs, caps or sleeves of different diameters to fit a range of femoral hollow sizes. They also may be formed of materials having different resorbabilities, stiffnesses or strengths for affecting load or strain distribution. This enables a surgeon to assemble or modify during the course of a surgical procedure a configuration and size of a prosthesis that is best for a given patient at the time of implant. Over time, and after implantation, the properties of the implant change as the second component is resorbed and the overall mechanical properties of the compound prosthesis and its attachments evolve.

In an illustrative implementation, a hip prosthesis has a femoral stem with metal stem body and a biocompatible and bio-absorbable second component installed at a distal end of the stem. The configuration and dimensions of the bio-absorbable component are such that it has a diameter that is greater than the nominal diameter of the first component of the hip stem, and fits a bore made by one of the standard size femoral canal straight or tapered bone reamers. The second component provides a distally tight fit at the time of implantation and augments the stem to provide a relatively rigid structure. However, after implantation, the distal end bio-absorbable component resorbs, increasing distal flexibility. During this post-implantation phase, new bone growth concurrently provides a more rigid attachment at the proximal end. The less rigid shaft thereby shifts its load and strain distribution so that an increasing portion of the load is applied at the femoral metaphysis and is carried by the intermediate portion of the natural femur. This results in a more natural loading of the femur with a strain distribution that counteracts bone atrophy and resorption. Thus, the modular construction largely avoids bone stress shielding.

The bio-absorbable component itself need not have recesses, and may take various forms such as a coating, wedge, plug, cap, sleeve or insert. In general it serves both to provide initial fit, and to control or guide the speed and extent of bone ingrowth. These two functions may be achieved with a modular component. Alternatively, separate isolated bio-absorbable portions, having the same or different resorption and growth characteristics, may implement both or primarily a single one of these functions. For achieving initial fit and fixation, the second component may include projections such as blade-like fins oriented along a direction of insertion, that, upon insertion, provide an irrotational "scratch fit" against surrounding bone. It may have one or more wing-like projections for anchoring or positioning the body. Furthermore, the bioabsorbable component need not be a separate modular piece, but may include a mass of irregular topology that extends into and through recesses or tunnels in the first, structural component, and projects outward therefrom to provide the initial external fit and a subsequent dissolution path for natural bone ingrowth. In this case the mass may be molded in situ, for example by using a deformable or viscous organic polymer, with a degree of cross-linking or hardening tailored to achieve the desired resorption time. Similarly, the second component may include coatings at one or more regions of the prosthesis, positioned to either enhance an initial interference fit, or promote later bone growth, together with separate, modular attachments.

Advantageously by providing a bio-absorbable and a metal component together in a compound or modular prosthesis, applicant separately and independently tailors the initial and ultimate values of fixation strength, strain transfer and bending stiffness of the prosthesis at two or more positions along the device. This new architecture achieves a high degree of initial fixation and strength without sacrificing the mechanical characteristics required for long term bone growth and compatibility.

BRIEF DESCRIPTION OF THE DRAWINGS

These and other features of the invention will be understood from the description below together with illustrative examples and drawings, wherein:

FIG. 2B is a sectional view of the prosthesis of FIG. 1 along lines 2B—2B;

FIG. 2C is a sectional view of the prosthesis of FIG. 1 along lines 2C—2C;

FIG. 3 shows another embodiment of a prosthesis in accordance with the present invention;

FIG. 3A is a sectional view of the prosthesis of FIG. 3 along lines 3A—3A;

FIG. 3B is a sectional view of the prosthesis of FIG. 3 along lines 3B—3B;

FIG. 4 is a further embodiment of a prosthesis in accordance with the present invention;

FIG. 4A is a sectional view of the prosthesis of FIG. 4 along lines 4A—4A;

DETAILED DESCRIPTION OF THE INVENTION

Figure 1:
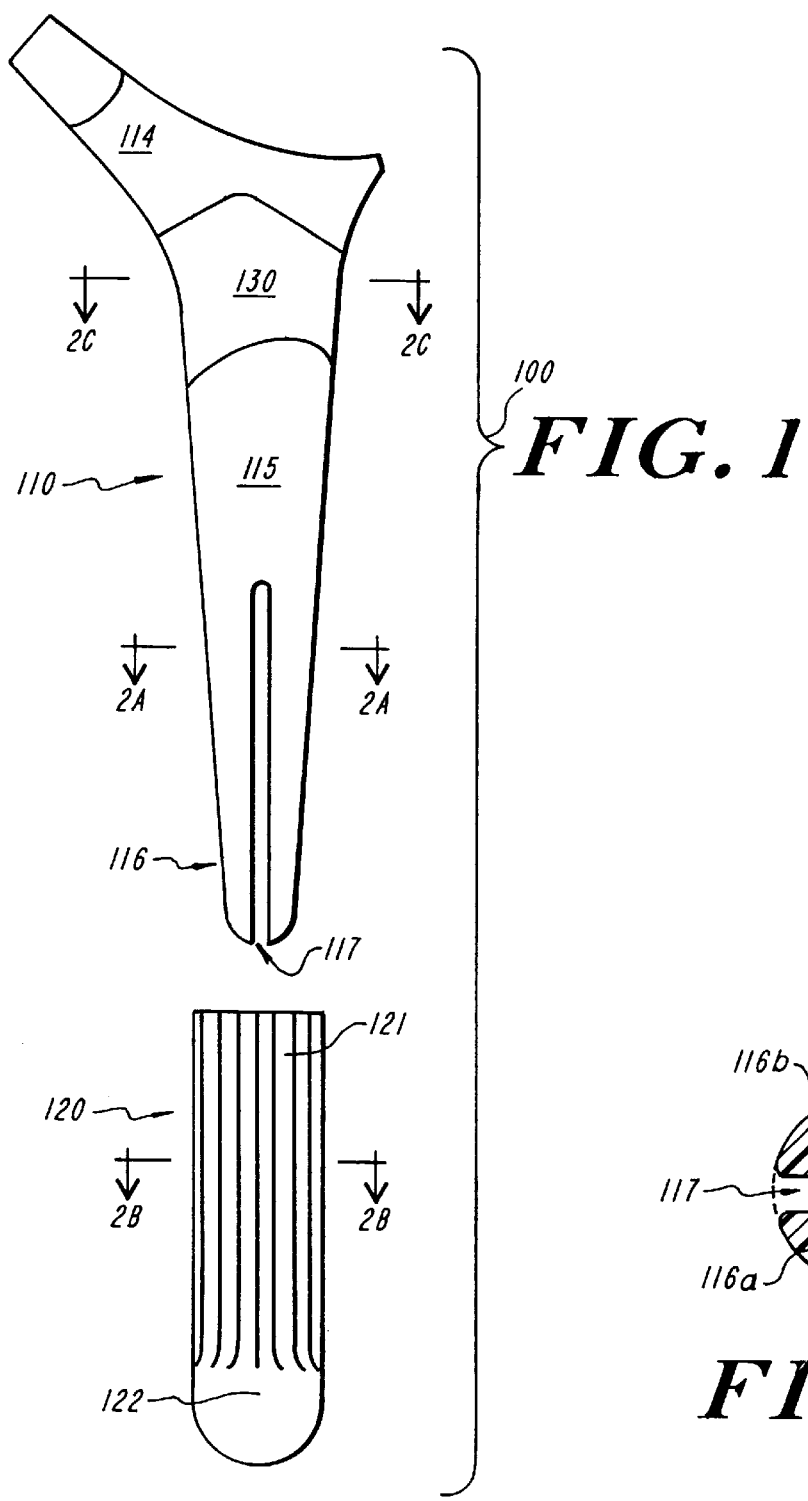
FIG. 1 shows a two-part modular prosthesis in accordance with the present invention.
Figure 2A:
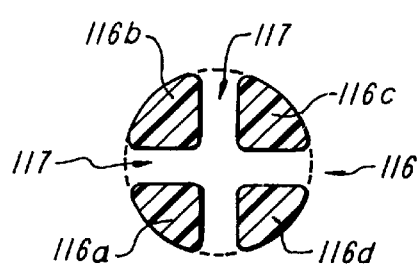
FIG. 2A is a sectional view of the prosthesis of FIG. 1 along lines 2A—2A.

FIG. 1 shows a side view of a hip prosthesis 100 according to a representative embodiment of the present invention. Prosthesis 100 includes an elongated body or structural part 110 and a distal cap or fitting part 120. The body 110 is adapted for insertion into the hollow center of a femur, and extends from a metaphyseal region 114 shown at the top in the drawing to a distal end 116, with the stem 115 in the intermediate portion being generally tapered along two planes in a known manner for fitting within the femur. The structural body 110 is formed of bio-compatible metals or alloys. Exemplary metals include cobalt and titanium, while exemplary alloys include $Ti_6Al_4V$ or CoCrMo. In the illustrated embodiment, the distal end 116 has the form of four separate elongated fingers 116a through 116d, shown in cross-section in FIG. 2A. Because of their relatively small cross section, these fingers 116a through 116d are capable of a relatively high degree of flexion or bending along their length in a manner similar to but of lesser magnitude than a clothespin. It will be understood that FIG. 1 is intended to show a generic external contour, which might be more rounded, more angular or otherwise correspond to known prostheses, and that as to the distal end, the FIGURE is a schematic representation only. That is, a person skilled in the art will understand that the actual contour of the fingers, particularly at their junction with the solid mid portion 115 of the stem, is to be configured to avoid the generation of stress cracks and provide a long and useful fatigue life of the prosthesis. In general however it will be noted that the shape of the distal end of the prosthesis involves deep grooves or entire through-slots 117 which separate the body of the stem into smaller more bendable beam-like structural portions.

The second component of the illustrated prosthesis is the distal end cap 120, one embodiment of which is shown in FIG. 1, and illustrated in cross section in FIG. 2B. Unlike the structural component 110, the end cap 120 is formed of a temporary material such as polylactic acid (PLA) or polydixanone (PDS), which is both bio-absorbable when implanted in the body, and is configured to extend beyond or protrude from the metal component of the distal stem portion. Suitable bio-absorbable materials include polyamino acids, polyacetates, polyglycolates, poly (p-dioxanone), co-condensates thereof, copolymers thereof, gelatin, collagen, and calcium phosphate-based materials. As illustrated, the cap 120 is an elongated sleeve which fits around the fingers 116a through 116d, and fills the gaps therebetween, resulting in a solid but compound, i.e., two-material, tip structure. The sleeve has a generally cylindrical portion 127 which fits around the stem, and a plurality of cross-bars 123, 125 or spoke-like members positioned to slide into the slots 117 of the body 110. The members 123, 125 may be dimensioned thicker than the slots 117, and may have a Shore D hardness selected such that by wedging into the slots 117, the members are placed under compression to couple the fingers 116 together. This rigidities the distal end 116 at the time of implantation. Thus, by filling the gaps between fingers, the resultant structure has a much higher bending stiffness than the metal component alone, while it attains a precise outer contour for enhanced fit to a size defined by the bio-absorbable component 120. Thus, both the diameter and the bending stiffness are augmented by the bio-absorbable component, and, significantly both of these structural properties decrease as component 120 is resorbed.

Of course, depending on the particular configuration of the gaps or negative surface features of the elongated body and the end cap, only a portion of the gaps or voids may be filled. In other embodiments the gaps or voids are substantially filled, and in yet other embodiments the gaps and voids are entirely filled. The bio-absorbable component can also protrude from the external surface of the femoral stem by a distance of about 0.001 inches to 0.250 inches, and more preferably by a distance of about 0.004 inches to 0.12 inches.

As shown generally in FIG. 1, the bio-absorbable component 120 of this embodiment fits like a sock or elongated cap over the distal end of the prosthesis and contains elongated ridges 121 oriented along the direction of insertion in the femur. The very end portion 122 lacks these relief features and instead provides a gently bulbous rounded surface for tightly fitting against a prepared bore formed in the femur. As further shown in FIG. 2B, the cross section of end sleeve 120 constitutes a segmented body configured to extend into the gaps or grooves 117 of the metal component, and firmly interlock with and fill that component to thus structurally augment it and provide an overall solid cross section of the prosthesis when the two components are assembled together. Slight protrusions or indentations 124 may also be provided internally to firmly lock the bio-absorbable component in place on the metal shaft.

As further shown in FIG. 1, the prosthesis 100 has an upper or metaphyseal fitting region 130 which is configured to contact surrounding bone. Conventionally, this region is fitted less precisely to the bone than the distal region, owing largely to the greater variation in size and shape of the femoral metaphysis. This region is fastened by a cement layer to surrounding bone, or is provided with a textured region and a coating to promote bone growth so that through this growth process ultimately the prosthesis later becomes rigidly coupled in its top portion directly to the femur.

FIG. 2C illustrates a horizontal cross section through the prosthesis in the region 130. As shown therein, the stem 110, illustratively a solid body, has an external coating 135 which as illustrated in FIG. 2C, is a thin shell or layer covering the bone contact and regrowth region in this metaphyseal area. It will be understood that this region may also be textured and have three dimensional relief features of a conventional kind to enhance trabecular bone growth and promote the long-term formation of a shear-free and irrotational coupling. So far as relevant hereto, any of the coating and texturing processes of the prior art may be applied to this region. In general, the large diameter and greater contact area in this region allow a very strong coupling to ultimately be achieved. However, as is well known in the art, when the healing process results in the prosthesis being firmly attached in the region 130 and remaining firmly attached at its distal end, the sharing of load between the prosthesis and surrounding bone can result in the intermediate portions of bone bearing very little load and being subjected to very little stress. This phenomena, known as bone stress shielding, is addressed in accordance with a principal aspect of the present invention by the provision of the bio-absorbable component 120 at the distal end which over time disappears or is replaced by new bone growth so that only the structural component 115 remains. As noted above, the distal end structural component has a low bending stiffness. For example, it may be subject to deflections of ten microns or more when subjected to a normal load caused by movement of the body. Furthermore, the outer shell 127 in some embodiments is compounded to resorb faster than it is replaced by new bone growth, so that once effective coupling has occurred in the metaphyseal region 130 the distal end may become free. This assures that intermediate portions of the femur will bear a high proportion of the load and that the bone will remain stressed in use. The long term loading of the femur effected after metaphyseal attachment in region 130 is therefore substantially similar to that of the natural bone.

FIGS. 3A and 3B illustrate other stem/cap configurations in which a bio-absorbable component 120' is configured to provide a high degree of initial fit and stability while allowing a metallic distal stem portion of lesser bending stiffness to reside permanently implanted. As shown in FIG. 3A, the sleeve 120' may be a roughly cylindrical sleeve which fits around a solid rod or shaft distal end portion of the metallic component. Like component 120 of FIGS. 1 and 2, this illustrated sleeve 120' has an outer surface with a plurality of blade-like protrusions 121' which extend radially outward, and may score the bone as the prosthesis is longitudinally inserted, to provide a secure grip against rotation of the implant. In this embodiment, a second bio-absorbable component 140 is separately fitted over the end of the sleeve 120', and has the shape of a bullet or plug having a fixed internal diameter matched to the sleeve 120'. The second component 140 is one of a set in which a modular selection of different size external diameters are configured for the different size bone reamers commonly used for prosthesis installation. The end block, bullet or plug 140 may be formed of a different material than the sleeve 120', and may, for instance, have faster or slower resorption characteristics, be provided with a loading of bone growth enhancement material, be made of a softer material to provide fit without increasing bending stiffness, or may otherwise be of a composition to specially tailor its resorption time and mechanical properties.

While each of the above embodiments has shown a separately-fitted distal component, FIG. 4 shows an embodiment wherein a bio-absorbable component 120" is noninterchangeably interfitted with the stem body. In this construction, the metal stem shaft is a tapered hollow cylindrical shell of undulating, polygonal or star-like shape, and the bioabsorbable component is interfitted or affixed to the stem in a more complex fashion to fill an interior region of the stem, for example, by an in situ molding or casting process rather than by assembly from modular components at the surgical site. As before, it extends outwardly to provide the initial areas of contact with surrounding bone.

FIG. 4A illustrates a cross-section of the stem, showing the interconnection of the bio-absorbable core and the structural shell. As before, a bullet-like end cap 150 similar to cap 140 may be provided for fit. This cap may be a separate item, or may be integrally formed with the component 120".

Figure 5:
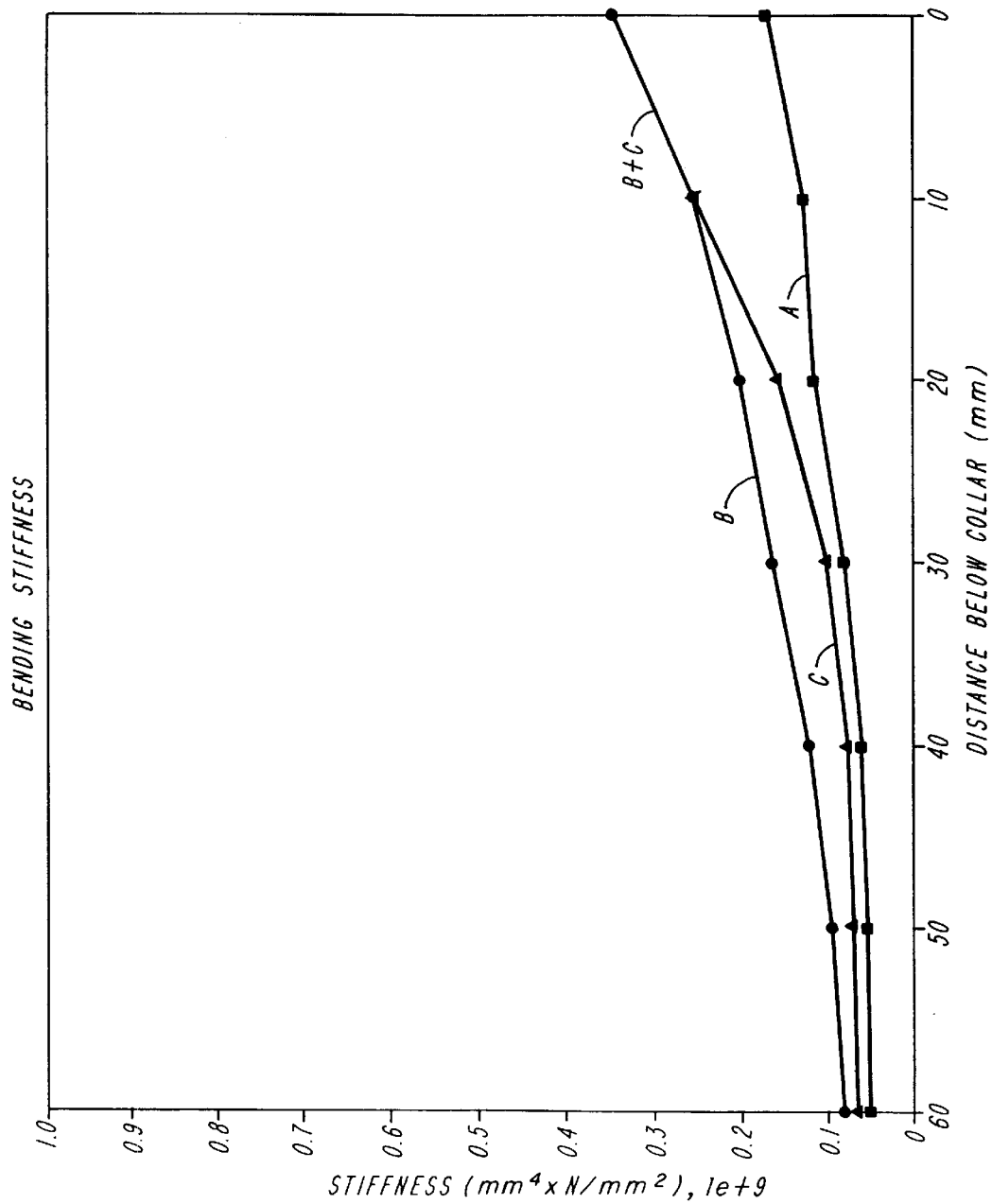
FIG. 5 shows representative bending stiffness of the prosthesis of FIGS. 1 or 3.
Figure 6:
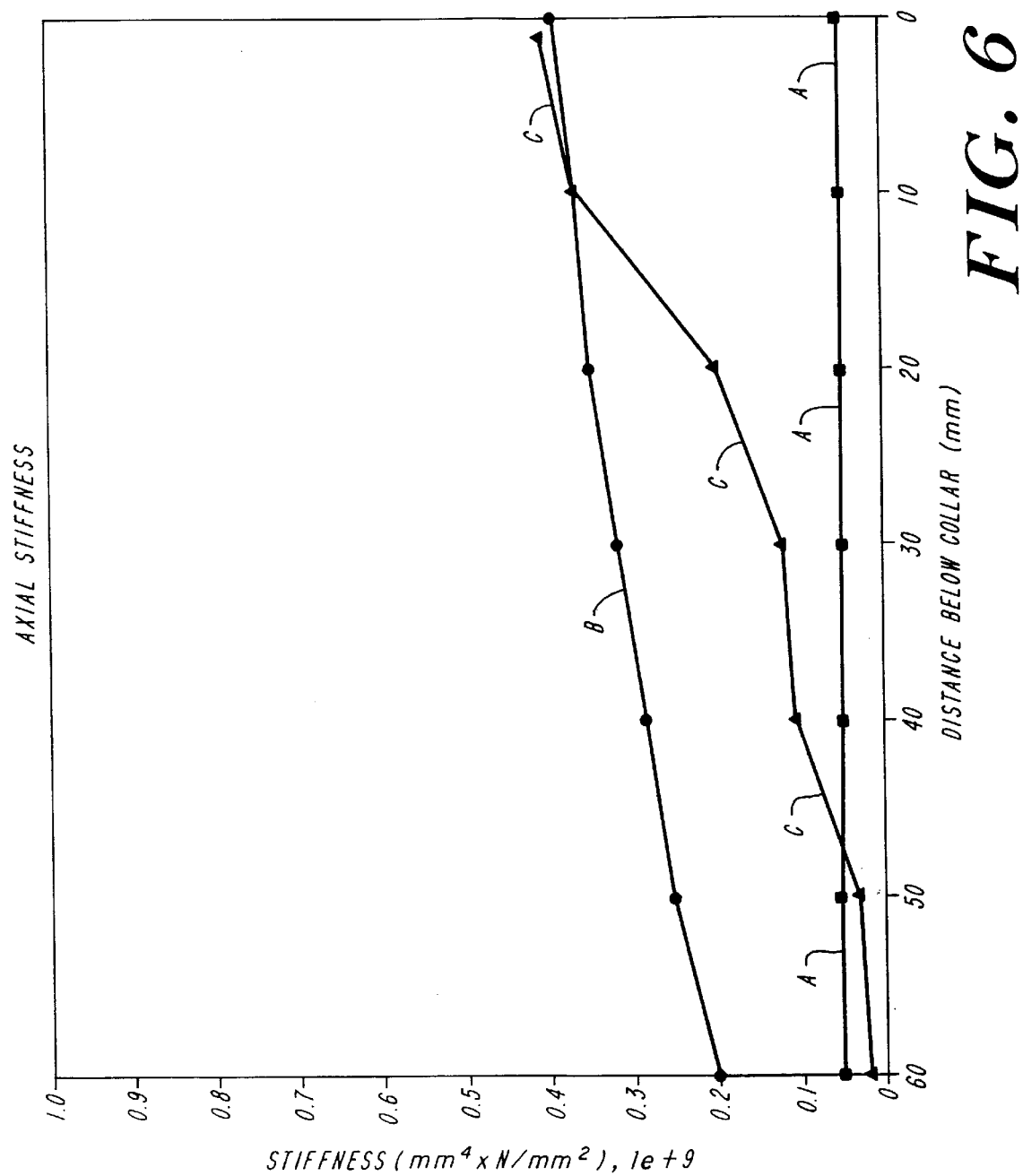
FIG. 6 is a conceptual graph illustrating the form of evolving stress distribution in bone.

As described above, the present invention advances the prior art engineering of bone prostheses by providing a structure in which the distal stiffness and fit evolve over time and, moreover, may follow different change function dictated by the physical structure of the stem, and by the modulus and "solubility" of the bio-absorbable components. Representative forms of the bending and axial stiffness are shown in FIGS. 5 and 6, respectively, at two points in time, indicated by curves "B" (initial implantation) and "C" (after implantation). The post-implantation curve is taken to be a time weeks or months later when both substantial distal component resorption and adequate metaphyseal regrowth have occurred. However, as noted above, each of these latter processes may be separately and independently modified by adjusting the compressibility and solubility of the non-metal portions and by use of appropriate growth promoters.

In both FIGS. 5 and 6, the stiffness of a representative natural femur is shown in curve A. In each case, the stiffness of the prosthesis upon implantation (curve B) is generally higher at all points along the prosthesis than that of the original bone. This is done simply to assure adequate overall strength in the immediate post-operative period while reducing the strain in the metaphyseal region to allow healing. However, time progress, as shown in curve C, the stiffness distribution shifts markedly. In particular, the bending stiffness in the distal region may be reduced to zero by employing a fast-resorbing polymer that completely disappears between the stem and surrounding bone by the time proximal end growth occurs. Alternatively, with a multi-finger embodiment as shown in FIGS. 1 and 2 and a slowly resorbed wedge component, a low but non-zero bending stiffness may be assured in that region over a protracted time. A range band around curve C indicates these design features.

It must be understood that the illustrated values are merely representative of an exemplary embodiment of the invention and that the values will vary considerably depending upon the configuration and materials selected. However, in one configuration, resorption of the bioabsorbable component reduces bending stiffness of the distal region of the prosthesis to under approximately $0.1e^{+9}$ mm4 (N/mm$^2$).

As further shown in these Figures, the proximal stiffness may remain relatively constant, with the only change being a result of degree of attachment in that region, so that curves B and C are substantially identical. Alternatively, if stiffness is provided by filling or augmenting a hollow shell in the metaphyseal region, the stiffness may decrease as the filler is resorbed, so that the stiffness of the regrown bone with prosthesis body is comparable to that of the filled prosthesis, and after implantation, load becomes transferred primarily through bone. In this case, each end of the prosthesis changes its actual stiffness to accommodate the burden taken up or released by the regrowth of bone and the changes in the other end of the prosthesis.

The invention being thus described, its structure and operative methods of practice will be readily applied and adapted to diverse known prosthesis constructions, and further variations and modifications will occur to those skilled in the art. All such adaptations, variations and modifications are considered to be within the scope of the invention, as set forth in the claims appended hereto.

What is claimed is:

1. A joint prosthesis, comprising:
   a metallic structural component adapted to fit within a cavity formed in existing bone;
   a negative surface feature formed in the metallic structural component; and
   a solid bio-absorbable component filling at least some of the negative surface feature, wherein the structural component is a shell having a longitudinal axis and the negative surface feature includes a tunnel formed in the shell that is parallel to the longitudinal axis.

2. A joint prosthesis, comprising:
   a metallic structural component adapted to fit within a cavity formed in existing bone;
   a negative surface feature formed in the metallic structural component; and
   a solid bio-absorbable component filling at least some of the negative surface feature, wherein the metallic structural component is substantially elongate and the negative surface feature is defined by a plurality of fingers at the distal end of the metallic structural component and two perpendicular through-slots are formed in the metallic structural component.

3. A joint prosthesis, comprising:
   a metallic structural component adapted to fit within a cavity formed in existing bone;
   a negative surface feature formed in the metallic structural component; and
   a solid bio-absorbable component filling at least some of the negative surface feature, wherein the bio-absorbable component includes a distal cap that is adapted to fit over a distal end of the metallic structural component to engage and interlock with at least a portion of the negative surface feature.

4. A joint prosthesis, comprising:
   a metallic structural component adapted to fit within a cavity formed in existing bone;
   a negative surface feature formed in the metallic structural component; and a solid bio-absorbable component filling at least some of the negative surface feature, wherein the negative surface feature includes at least one axially oriented elongate slot disposed in the distal end of the metallic structural component to form a femoral stem having a discontinuous distal end, and the bio-absorbable component is a distal cap that is adapted to engage and interlock with at least a portion of the negative surface feature fitting over the distal end of the metallic structural component to fill and strengthen the stem.

5. The joint prosthesis of claim 4, wherein the bio-absorbable component protrudes from an external surface of the femoral stem by a distance of about 0.001 inches to 0.250 inches.

6. The joint prosthesis of claim 4, wherein the bio-absorbable component protrudes from an external surface of the femoral stem by a distance of about 0.004 inches to 0.12 inches.

7. A joint prosthesis, comprising:
- a metallic structural component adapted to fit within a cavity formed in existing bone;
- a negative surface feature formed in the metallic structural component; and
- a solid bio-absorbable component filling at least some of the negative surface feature, where resorption of the bio-absorbable component reduces bending stiffness of the distal region of the prosthesis to under approximately $0.1e^{+9}$ mm4 (N/mm$^2$).

* * * * *